US010376682B2

(12) United States Patent
Hwang et al.

(10) Patent No.: US 10,376,682 B2
(45) Date of Patent: Aug. 13, 2019

(54) METHOD OF MANUFACTURING AN IMPLANTABLE PRESSURE-ACTUATED DRUG DELIVERY SYSTEM

(71) Applicant: The Johns Hopkins University, Baltimore, MD (US)

(72) Inventors: Chao-Wei Hwang, Ellicott City, MD (US); Hala J. Tomey, Washington, DC (US); Jon R. Resar, Stevenson, MD (US); Robert C. Matteson, III, Ellicott City, MD (US); George L. Coles, Jr., Baltimore, MD (US); Jason J. Benkoski, Ellicott City, MD (US); Morgana M. Trexler, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 413 days.

(21) Appl. No.: 15/290,129

(22) Filed: Oct. 11, 2016

(65) Prior Publication Data

US 2017/0028181 A1    Feb. 2, 2017

Related U.S. Application Data

(62) Division of application No. 14/179,835, filed on Feb. 13, 2014, now Pat. No. 9,504,586, which is a division
(Continued)

(51) Int. Cl.
*A61M 31/00* (2006.01)
*A61F 2/82* (2013.01)
(Continued)

(52) U.S. Cl.
CPC ............. *A61M 31/002* (2013.01); *A61F 2/82* (2013.01); *A61K 9/0012* (2013.01);
(Continued)

(58) Field of Classification Search
CPC ........ A61M 31/002; A61M 25/10; A61K 9/11
See application file for complete search history.

(56) References Cited

U.S. PATENT DOCUMENTS 5,366,454 A * 11/1994 Currie ................. A61M 31/002
                                                    137/68.19
5,845,646 A    12/1998 Lemelson
(Continued)

FOREIGN PATENT DOCUMENTS

| WO | 9303696    | 4/1992 |
| WO | 2004026281 | 4/2004 |
| WO | 2007042961 | 4/2007 |

OTHER PUBLICATIONS

Boden W.E. et al., Optimal Medical Therapy with or without PCI for Stable Coronary Disease, The New England Journal of Medicine, Apr. 12, 2007, vol. 356 No. 15, pp. 1503-1516.
(Continued)

*Primary Examiner* — Dah-Wei D. Yuan
*Assistant Examiner* — Andrew J Bowman
(74) *Attorney, Agent, or Firm* — Noah J. Hayward

(57) ABSTRACT

Implantable pressure-actuated systems to deliver a drug and/or other substance in response to a pressure difference between a system cavity and an exterior environment, and methods of fabrication and use. A pressure-rupturable membrane diaphragm may be tuned to rupture at a desired rupture threshold, rupture site, with a desired rupture pattern, and/or within a desired rupture time. Tuning may include material selection, thickness control, surface patterning, substrate support patterning. The cavity may be pressurized above or evacuated below the rupture threshold, and a diaphragm-protective layer may be provided to prevent premature rupture in an ambient environment and to dissipate within an implant environment. A drug delivery system may be implemented within a stent to release a substance upon a decrease
(Continued)

in blood pressure. The cavity may include a thrombolytic drug to or other substance to treat a blood clot.

10 Claims, 12 Drawing Sheets

Related U.S. Application Data of application No. 12/985,015, filed on Jan. 5, 2011, now Pat. No. 8,696,740.

(60) Provisional application No. 61/292,339, filed on Jan. 5, 2010.

(51) Int. Cl.

| | | |
|---|---|---|
| *A61K 9/00* | (2006.01) | |
| *A61L 31/16* | (2006.01) | |
| *A61L 31/14* | (2006.01) | |
| *A61L 33/00* | (2006.01) | |
| *B05D 1/00* | (2006.01) | |
| *C23C 14/22* | (2006.01) | |

(52) U.S. Cl.
CPC .......... *A61K 9/0024* (2013.01); *A61K 9/0097* (2013.01); *A61L 31/145* (2013.01); *A61L 31/16* (2013.01); *A61L 33/0017* (2013.01); *B05D 1/005* (2013.01); *C23C 14/22* (2013.01); *A61F 2240/001* (2013.01); *A61F 2250/0068* (2013.01); *A61F 2250/0071* (2013.01); *A61L 2300/42* (2013.01); *A61L 2300/602* (2013.01); *A61L 2300/606* (2013.01); *A61L 2420/02* (2013.01); *Y10T 29/49826* (2015.01)

(56) References Cited

U.S. PATENT DOCUMENTS

| | | |
|---|---|---|
| 6,231,516 B1 | 5/2001 | Keilman et al. |
| 6,491,666 B1 | 12/2002 | Santini et al. |
| 6,546,232 B1 | 4/2003 | Sack et al. |
| 6,970,737 B1 | 11/2005 | Brodnick et al. |
| 7,041,130 B2 | 5/2006 | Santini et al. |
| 7,232,460 B2 | 6/2007 | Van Erlach et al. |
| 7,236,821 B2 | 6/2007 | Cates et al. |
| 7,534,241 B2 | 5/2009 | Coppeta et al. |
| 7,580,746 B2 | 8/2009 | Gilkerson et al. |
| 7,582,080 B2 | 9/2009 | Santini et al. |
| 7,875,072 B2 | 1/2011 | Spielberg et al. |
| 8,187,221 B2 | 5/2012 | Bates |
| 8,211,092 B2 | 7/2012 | Uhland et al. |
| 8,684,968 B2 | 4/2014 | Genosar |
| 9,107,605 B2 | 8/2015 | Boyle et al. |
| 2003/0050692 A1 | 3/2003 | Sirhan et al. |
| 2003/0100865 A1 | 5/2003 | Santini et al. |
| 2004/0106953 A1 | 6/2004 | Yomtov et al. |
| 2005/0000514 A1 | 1/2005 | Sullivan et al. |
| 2006/0129050 A1 | 6/2006 | Martinson et al. |
| 2008/0063703 A1 | 3/2008 | Gross et al. |
| 2009/0082652 A1 | 3/2009 | Koh et al. |
| 2010/0069888 A1 | 3/2010 | Solomon |
| 2010/0087778 A1 | 4/2010 | Genosar et al. |
| 2010/0185038 A1 | 7/2010 | Uhland et al. |
| 2011/0282426 A1 | 11/2011 | Mitra et al. |
| 2012/0150142 A1* | 6/2012 | Weber ..................... A61L 29/08 604/500 |
| 2015/0182145 A1 | 7/2015 | Gazdzinski |

OTHER PUBLICATIONS

Edelman E.R. et al., Optimization of Release from Magnetically Controlled Polymeric Drug Release Devices, Biomaterials 1993, vol. 14 No. 8, pp. 621-626.
Finn A.V. et. al., Vascular Responses to Drug Eluting Stents: Importance of Delayed Healing, Arterioscler Thromb Vasc Biol 2007, vol. 27, pp. 1500-1510.
Jaffe R. et al., Late and Very Late Thrombosis of Drug-Eluting Stents: Evolving Concepts and Perspectives, Journal of the American College of Cardiology, vol. 50, No. 2, 2007, pp. 119-127.
Kwok C.S. et al. Self-Assembled Molecular Structures as Ultrasonically-Responsive Barrier Membranes for Pulsatile Drug Delivery, Student Research Award in the Doctoral Degree Candidate Category, 27th Annual Meeting of the Society for Biomaterials, St. paul, MN, 2001, pp. 151-164.
Kwon I.C. et al., Electrically Erodible Polymer Gel for Controlled Release of Drugs, Nature vol. 354, Nov. 28, 1991, pp. 291-293.
Prescott J. H. et al., Chronic, Programmed Polypeptide Delivery from an Implanted, Multireservoir Microchip Device, Nature Biotechnology vol. 24 No. 4, Apr. 2006, pp. 437-438.
Santini J. T. et al., A Controlled Release Microchip, Nature vol. 297, Jan. 28, 1999, pp. 335-338.
Sarkar K. et al., Coronary Artery Restenosis: Vascular Biology and Emerging Therapeutic Strategies, Expert Rev. Cardiovasc. Ther. 4(4), pp. 543-556.
Fornell D., Trends in Coronary, Carotid and Peripheral Stents, DI Cardiology, Sep. 18, 2009, pp. 1-3.
Ladisa J. Jr. et al., Axial Stent Strut Angle Influences Wall Shear Stress After Stent Implantation: Analysis Using 3D Computational Fluid Dynamics Models of Stent Foreshortening, BioMedical Engineering OnLin 2005, pp. 1-10.
Sershen K. et al., Polymeric Systems for Modulated Drug Delivery, Adv., Advanced Drug Delivery Review, Elsevier, Nov. 2002, pp. 1225-1235.
Tsivgoulis G. et al., Utlrasound-Enhanced Thrombolysis in Acute Ischemic Stroke: Potential, Failures, and Safety, Neurotherapeutics: The Journal of the American Society for Experimental Neuro Therapeutics, Jul. 2007, pp. 420-427.
International Bureau, "Preliminary Report on Patentability," International Application No. PCT/US2011/027180 (corresponds to instant U.S. Appl. No. 12/985,015), dated Sep. 19, 2013, 8 pages.

* cited by examiner

METHOD OF MANUFACTURING AN IMPLANTABLE PRESSURE-ACTUATED DRUG DELIVERY SYSTEM

CROSS REFERENCE TO RELATED APPLICATIONS

This application a divisional of co-pending U.S. Nonprovisional patent application Ser. No. 14/179,835 filed on Feb. 13, 2014, which is a divisional of U.S. Nonprovisional patent application Ser. No. 12/985,015 filed on Jan. 5, 2011, now U.S. Pat. No. 8,696,740, which claims priority to and the benefit of U.S. Provisional Patent Application Ser. No. 61/292,339, filed on Jan. 5, 2010 (now expired), the entire contents of each of which are herein incorporated by reference in their entireties.

BACKGROUND

Technical Field

Mechanically actuated substance delivery methods and systems, including implantable, pressure-actuated drug delivery methods and systems.

Related Art

Coronary stents are commonly used to treat heart attacks. Stents, however, have been known to abruptly clot. Conventional stent clot treatment includes emergency angioplasty, which is expensive, difficult to coordinate, and accompanied by relatively high mortality rates.

Stents have been coated with drugs ("drug-eluting stents") to reduce the formation of scar tissue. However, drug-eluting stents have been shown to increase the likelihood of abrupt in-stent clot formation.

Stents have been textured and coated with antibodies and proteins to attract native cell coverings in attempts to promote vessel healing and reduce clot formation, without much success and, in some cases, with increased clotting. Furthermore, such passive systems are not able to sense nor adapt to new clots that may occur.

Conventional intracoronary drug-delivery systems are passive. Drugs are released with pre-determined kinetics, and these systems cannot sense nor respond to new, abrupt environmental changes such as clotting. Active drug delivery systems deliver drugs in response to an external stimulus, but conventional systems require a bulky or externalized power source, a separate sensor and are unsuitable for intracoronary application. For example, World Intellectual Property Organization (WIPO) publication number WO 2007/042961, to Johnson et al., teaches a substrate having a chemical containing reservoir sealed with a rupturable barrier layer (Johnson, page 2, lines 18-26), including a polymer layer and a metal layer (Johnson, page 6, lines 1-10), and an "inkjet printer and/or hydraulic system (i.e., a fluid pressure system with controlled release valves)," or a "piezo-electrical means, e.g. a piezoactuator and/or loudspeaker," (Johnson, page 5, lines 21-29), to rupture the barrier layer.

What are needed are small-scale, implantable, minimally invasive, and mechanically actuated drug delivery methods and systems that do not require an external power source or a separate sensor.

SUMMARY

Disclosed herein are implantable pressure-actuated systems to deliver a drug and/or other substance in response to a pressure difference between a system cavity and an exterior environment, and methods of fabrication and use.

A pressure-rupturable membrane or diaphragm may be tuned to rupture at a desired rupture threshold, rupture site, with a desired rupture pattern, and/or within or after a desired rupture time. The diaphragm may be tuned by selection of material, controlling a thickness, patterning a surface, patterning an underlying substrate support, and/or changing the material composition of the diaphragm.

The cavity may be pressurized above or evacuated below the rupture threshold, and a diaphragm-protective layer may be provided to prevent premature diaphragm rupture in an ambient environment and to dissipate within an implant environment. The cavity may be pressurized above an implant environment pressure, such as a blood vessel pressure. Under normal conditions, diaphragm integrity is maintained by counteracting pressure of the implant environment. When the counteracting pressure of the implant environment falls, such as loss of blood pressure due to an occlusive blood clot, and the pressure difference across the diaphragm falls, the diaphragm ruptures and the drug and/or other substance is released or delivered into the implant environment.

The drug and/or other substance may include, without limitation, a thrombolytic, plasminogen, plasmin, heparin, and/or other anti-thrombotic agent, antiplatelet agent, anti-inflammatory agent, immunomodulator, and/or other enzyme or protein, DNA, RNA, mRNA and/or other genetic material, virus particles, cells, small molecule, anti-lipid agent, and/or medication.

Methods and systems disclosed herein may be implemented alone and/or in combination with one or more other implant platforms, such as a stent, including a coronary and a non-coronary or peripheral stent.

BRIEF DESCRIPTION OF THE DRAWINGS/FIGURES

Figure 1:
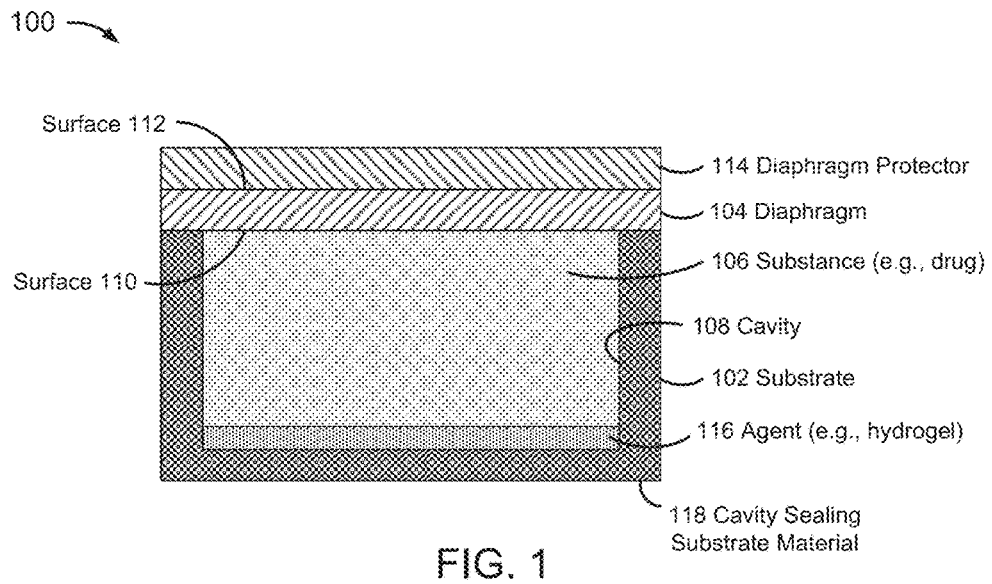
FIG. 1 is a block diagram of a pressure-actuated drug delivery system, including a substrate and a pressure-rupturable diaphragm to releasably retain a drug within a cavity of the substrate.

In the drawings, the leftmost digit(s) of a reference number identifies the drawing in which the reference number first appears.

DETAILED DESCRIPTION

FIG. 1 is a block diagram of a pressure-actuated drug delivery system 100, including a substrate 102 and a pressure-rupturable diaphragm 104 to releasably retain a drug 106 within a cavity 106 of substrate 102.

Diaphragm 104 may be configured to rupture upon a pre-determined pressure difference across first and second surfaces or sides 110 and 112, referred to herein as a rupture threshold. A pressure on surface 110 may be a pre-determined pressure, which may be set during fabrication and/or prior to or at the time of implantation. A pressure on surface 112 may correspond to an implant environment pressure, such as a vascular blood pressure.

The rupture threshold may be a function of a material and physical characteristics of diaphragm 104. Physical characteristics may include thickness, and/or other physical features of diaphragm 104. For example, surface 112 may have ridges, walls, posts, grooves, depressions, and/or other physical features formed therein, which may served to anchor and/or stiffen diaphragm 104. Physical characteristics of diaphragm 104 may be configured to control the rupture threhsold, and may be designed with assistance of a finite element analysis (FEA).

The rupture threshold may further be a function of substrate features within cavity 108, such as described in examples below.

Material and/or physical characteristics of diaphragm 104 and/or substrate features within cavity 108 may also be configured to control a rupture site, rupture pattern, and/or rupture time, such as described in examples below.

Diaphragm 104 may include one or more layers or films of one or more materials to form a frangible layer.

Substrate 102 and diaphragm 104 may be fabricated from one or more materials that remain relatively stable within an implant environment for at least a pre-determined time, referred to herein as an operating life of system 102, and may include a material that will remain relatively stable within the implant environment beyond the operating life. Stability may be measured in terms of dissolution, biodegradation, dissipation, and/or corrosion within the implant environment.

For example, the American Heart Association recommends treating stent patients with clopidogrel (a blood thinner) for one year following stent implantation to provide the blood vessel sufficient time to heal. Several pathology studies suggest that, at least with respect to animals, a stented blood vessel may need up to two or more 2 years to heal.

Where system 100 is implemented within a stent, substrate 102 and diaphragm 104 may thus be fabricated from one or more materials that will remain relatively stable within a blood vessel for up to one year, up to two years, or longer. Methods and systems disclosed herein are not, however, limited to a pre-determined period of time or an operating life.

Substrate 102 and diaphragm 104 may be fabricated, for example, from one or more metals and/or non-metal materials. A metal may include, without limitation, one or more of chromium, titanium, nickel, cobalt, gold, tungsten, and/or combinations and/or alloys thereof A non-metal material may include, without limitation, silicon dioxide and/or other a silicon compound, and/or a polymer that remains stable over the operating life, which may include a polylactic or polyglycolic acid.

Substrate 102 may include a silicon substrate, and diaphragm 104, or portions thereof, may be spin-coated and/or deposited by electron-beam evaporation onto a surface of substrate 102, such as described in one or more examples below. Physical features may be imparted to diaphragm 104, such as with photo-lithographic etching, such as described in one or more examples below.

Cavity 108 may be pressurized and/or evacuated based on an implant environment, and diaphragm 104 may be configured with a rupture threshold based on a potential adverse pressure change within the implant environment. Cavity 108 may be pressurized to a pressure substantially equal to a sum of a desired rupture pressure and a rupture threshold of diaphragm 104. Conversely, the rupture pressure may be defined as a difference between the cavity pressure and the rupture threshold.

Where system 100 is implanted within a blood vessel, for example, normal physiological blood pressure maintains sufficient pressure against diaphragm surface 112 to prevent rupture. In the event of an occlusive blood clot, counteracting physiological blood pressure at diaphragm surface 112 may fall below the pre-determined rupture pressure, which may cause diaphragm 104 to rupture and release drug 106 and/or other substance into the blood vessel to contact the clot. Drug 106 may include one or more drugs to mechanically disrupt and/or enzymatically degrade the clot, which may re-establish blood flow.

Example pressure values are provided below with respect to a blood vessel implant environment and an example rupture threshold. Methods and systems disclosed herein are not, however, limited to any of the pressure values or the implant environment of the examples below. In the examples below, pressure values are provided below in millimeters of mercury (mmHg), relative to one (1) atmosphere.

A normal systolic blood pressure may be within a range of approximately 100-140 mmHg.

A normal diastolic blood pressure may be within a range of approximately 70-90 mmHg.

A lowered blood pressure indicative of a distal clot may be within a range of approximately 5-20 mmHg.

Cavity 108 may be pressurized based on a desired rupture pressure (e.g., a lowered blood pressure), and a diaphragm rupture threshold.

The desired rupture pressure may be patient specific and/or implant location specific, and may be determined in consultation with a medical professional. A desired rupture pressure may be, for example, approximately 40 mmHg.

A rupture threshold of an example chromium based diaphragm may be approximately 300 mmHg.

Cavity 108 may thus be pressurized to approximately at 340 mmHg to cause diaphragm 104 to rupture when the blood pressure falls below 40 mmHg.

In other examples, cavity 108 may be pressurized to less than or greater than 340 mmHg, including less than or equal to 300 mmHg, greater or equal to 1000 mmHg, and may be within a range of approximately 300 mmHg to 1000 mmHg, within a range of approximately 200 mmHg to 1200 mmHg, or may be evacuated, depending upon the desired rupture pressure and the rupture threshold.

In other examples, diaphragm 104 may be fabricated and/or subsequently configured to provide a rupture threshold less than or greater than 300 mmHg, including less than or equal to 200 mmHg, less than or equal to 1200 mmHg, and may be within a range of approximately 200 mmHg to 1200 mmHg.

In other examples, a rupture pressure may be greater or less than 40 mmHg, including less than or equal to 20 mmHg, less than or equal to 50 mmHg, and may be within a range of approximately 20 mmHg to 50 mmHg.

Diaphragm 104 may be fabricated and/or subsequently configured to rupture substantially immediately upon exposure to a rupture pressure. Alternatively, diaphragm 104 may be fabricated and/or subsequently configured to maintain integrity when exposed to the rupture pressure for less than a pre-determined period of time, and to rupture after exposure to the rupture pressure for at least a pre-determined period of time. Such a pre-determined period of time is referred to herein as a rupture time. Delayed rupture may be useful, for example, to prevent rupture due to a spurious condition, such as a spurious drop in blood flow that may not be indicative of a blood clot. Diaphragm 104 may be fabricated and/or subsequently configured to rupture upon exposure to a rupture pressure of, for example, within 5 seconds, after at least 5 seconds, within 15 second, after at least 15, within 60 seconds, or after at least 60 seconds or more.

System 100 may include a dissolvable and/or bio-degradable diaphragm protector 114 disposed over second surface 112 of diaphragm 104, which may be configured to prevent premature rupture of diaphragm 104. Diaphragm protector 114 may be useful to protect diaphragm 104 from rupture prior to implantation, such as where an ambient or pre-implant environment pressure is below the rupture pressure.

Diaphragm protector 114 may include one or more water-soluble and/or bio-degradable materials, such that diaphragm protector 114 substantially dissolves, bio-degrades, or otherwise dissipates within an implant environment. Diaphragm protector 114 may include, for example, a water-soluble polymer, and may include one or more relatively long chain polyethylene glycols of varying molecular weights. Alternatively, or additionally, diaphragm protector 114 may include a biodegradable polymer, such as a polylactic and/or polylactic-co-glycolic acid.

The material of diaphragm protector 114 may be spun onto diaphragm surface 112 to a thickness sufficient to protect diaphragm 104 from mechanical and pressure-related damage during fabrication, storage, shipping, and/or implantation. Diaphragm 104 may have a thickness of, for example, greater than 10 micrometers (um).

When system 100 is implanted, diaphragm protector 114 dissolves, degrades, and/or otherwise dissipates to expose diaphragm surface 112 to the implant environment.

Drug 106 within cavity 108 may include, without limitation, a thrombolytic, plasminogen, plasmin, heparin, and/or other anti-thrombotic agent, antiplatelet agent, anti-inflammatory agent, immunomodulator, and/or other enzyme or protein, DNA, RNA, mRNA and/or other genetic material, virus particles, cells, small molecule, anti-lipid agent, and/or medication.

Drug 106 and/or cavity 108 may include one or more compounds or agents 116 applied to a surface of cavity 108 and/or within an interior portion of cavity 108.

Agent 116 may include a swelling agent to expand upon contact with a fluid, which may help to expel drug 106 from cavity 108 into the implant environment. The swelling agent may expand to occupy all or substantially all of cavity 108. The swelling agent may include a hydrogel, such as a drug-eluting hydrogel, which may include one or more of an anti-coagulant, such as heparin, a thrombolytic, and/or other drug.

Agent 116 and/or drug 106 may include an indicator to alert the patient when membrane 104 releases drug 106. The indicator may include, for example, allyl methyl sulfide, a compound that provides a garlic sensation.

Drug delivery system 100 may be implemented as a stand-alone implantable platform, and/or may be affixed to, embedded with, and/or integrated within another implantable platform. Drug delivery system 100 may, for example, be embedded within wells of a metal ring and/or a stent to be implanted within a vascular passage.

Drug delivery system 100 may be implemented, for example, as part of a coronary and/or non-coronary stent. Non-coronary stents may be implemented to treat non-coronary vessels, such as carotid, renal, subclavian, aorta, femoral, popliteal, iliac and other arteries. System 100 may be implemented, for example, to treat peripheral artery disease (PAD), which may affect femoral, popliteal, iliac and other arteries. Non-coronary stents are also referred to herein as peripheral stents and PAD stents. Peripheral stents may need more flexibility than coronary stents because lesions may be longer and may be located between muscle and bone in the legs, which may place greater stress and torque on a stent. To reduce the chance of displacement, fracture, and/or crushing of stents, a peripheral stent may be implemented as a self-expanding stent, and may be manufactured from a relatively flexible nickel-titanium alloy developed by the U.S. Naval Ordinance Lab, commercially known as Nitinol, an acronym for Nickel Titanium Naval Ordinance Laboratory.

Where drug delivery system 100 is incorporated within a stent, the stent may be implanted within an vessel, such as a coronary artery, using conventional percutaneous techniques. Once implanted, drug delivery system 100 may operate without external sensory or control intervention.

Drug delivery system 100 may be implemented to treat heart attacks caused by occlusive coronary clots, and may be retroactively placed in a patient who has already received a stent. Other example implementations are provided below.

Drugs and/or endocrine conditions may lead to a critical rise in blood pressure. Drug delivery system 100 may be implemented to release anti-hypertensive drugs when blood pressure exceeds a pre-determined threshold.

Fluid overload in a patient suffering from heart failure may experience an increase in central venous pressure (CVP), which may be treated with diuretics. Drug delivery system 100 may be implemented to release diuretics when the CVP exceeds a pre-determined threshold.

Patients with end-stage renal disease and who are on dialysis may experience clotting of an arteriovenous conduit (fistula or graft). Drug delivery system 100 may be incorporated within the arteriovenous conduit to release thrombolytics to clear the clot from the conduit.

Anaphylaxis is a sudden allergic reaction that can cause a fatal drop in blood pressure. Drug delivery system 100 may be implemented to release epinephrine, corticosteroids and/or anti-histamines to prevent and/or ameliorate anaphylactic shock.

An acute rise in intracranial pressure may cause fatal brain herniation before emergency neurosurgical intervention can be performed. Drug delivery system 100 may be implemented to respond to intracranial pressure by releasing steroids and/or diuretics to provide additional time for neurosurgical decompression.

System 100 may be implemented to release vasopressants when blood pressure falls as a result of trauma, which may temporarily sustain blood pressure until medical assistance is provided.

System 100 may be implemented to repair a non-biological system, such as to release a liquid sealant to seal a puncture in response to a pressure change.

System 100 may include a layer or membrane laced with a high-resistivity heating wire, such as nickel-chromium alloy wire. The coil may be inductively heated with a magnetic resonance coil to melt the membrane and expose diaphragm 104 and/or diaphragm protector 114. For example, with multiple instances of System 100 on a stent each with membranes of slightly different melting points, the stent will be able to function for multiple different episodes of stent clotting. Alternatively, a wire-laced membrane may be implemented as diaphragm 104.

Multiple instances of system 100 may be fabricated on a shared substrate, which may be cut into portions of one or more instances of system 100.

Subsets of instances of system 100 may be configured with different rupture thresholds, which may permit delivery of drugs in response to different environmental pressures.

Subsets of instances of system 100 may also be provisioned with different drugs and/or combinations of drugs, which may permit delivery of different drugs in response to different environmental pressures.

Subsets of instances of system 100 may include membranes having disparate melting points, such as different formulations of ethylene vinyl acetate copolymer, and the membranes may be laced with the high-resistivity heating wire described above to permit selective activation of the instances of system 100.

The shared substrate may be cut to provide an implantable substrate that includes multiple instances of system 100, which may include multiple rupture thresholds, multiple drugs and/or combinations of drugs, and/or membranes having disparate melting temperatures.

An ultrasound transducer may be implanted physically proximate to system 100 to emit signals at a resonant wavelength of cavity 108 to rupture diaphragm 104 with relatively minimal energy. The acoustic signals may have a wavelength substantially equal to integer multiple of 4L, where L is depth of cavity 106. The ultrasound transducer may be used as actuate drug delivery system 100 independently of an implant environment pressure, and/or may be used as a back-up actuator. The ultrasound transducer may be coupled to an ECG sensor to actuate drug delivery system 100 when the ECG sensor detects ST segment elevations.

Figure 2:
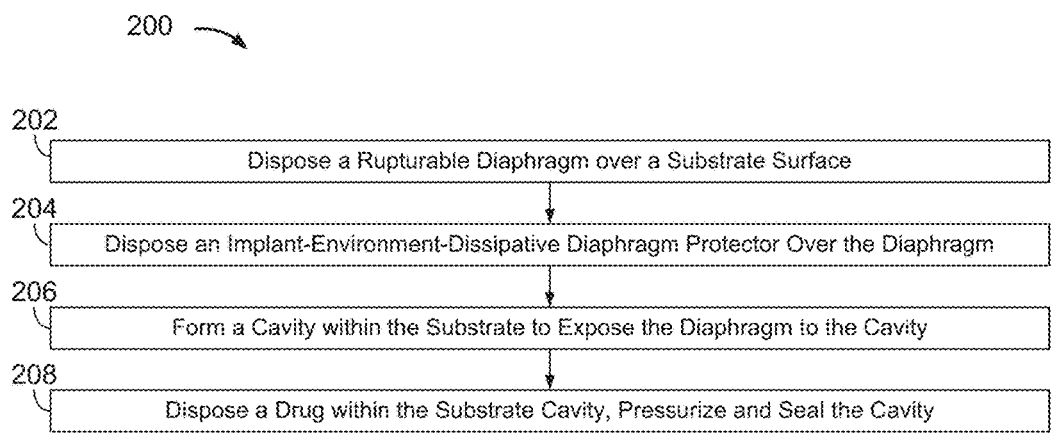
FIG. 2 is a flowchart of a method of fabricating a pressure-actuated drug delivery system.

FIG. 2 is a flowchart of a method 200 of fabricating a pressure-actuated drug delivery system. For illustrative purposes, method 200 is described below with reference to FIGS. 1 and 3 through 6. FIGS. 3-6 are graphic illustrations of stages of fabrication of drug delivery system 100. Method 200 is not however, limited to any of the examples of FIGS. 1 and 3 through 6.

Figure 3:
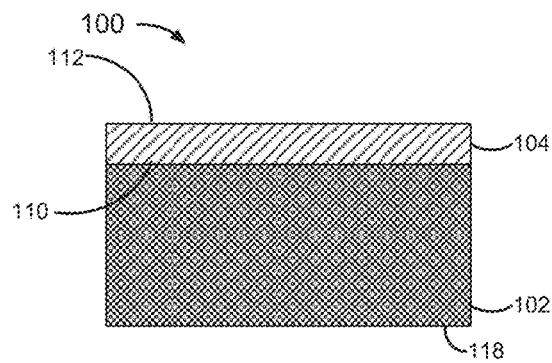
FIG. 3 is a graphic illustration of a fabrication stage of the drug delivery system of FIG. 1.

At 202, diaphragm 104 is disposed over a surface of substrate 102, as illustrated FIG. 3, such as by spin-coating and/or electron-beam deposition or evaporation.

Figure 4:
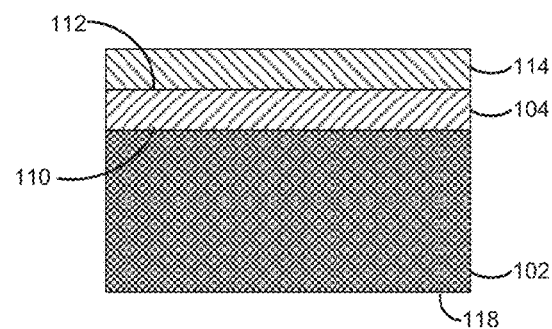
FIG. 4 is a graphic illustration of another fabrication stage of the drug delivery system of FIG. 1.

At 204, diaphragm protector 114 is disposed over diaphragm 104, as illustrated FIG. 4.

As described in examples below, diaphragm protector 114 may be disposed over diaphragm 104 subsequent to formation of cavity 108 at 206.

Figure 5:
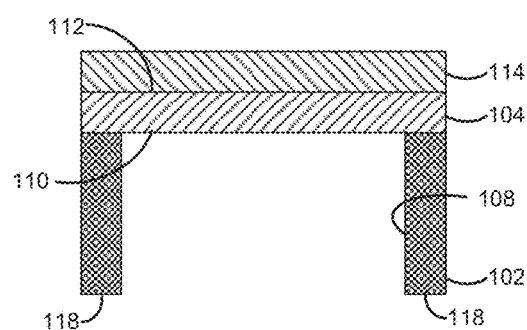
FIG. 5 is a graphic illustration of another fabrication stage of the drug delivery system of FIG. 1.

At 206, cavity 108 is formed within substrate 102, to expose at least a portion of diaphragm surface 110 to cavity 108, as illustrated FIG. 5.

Figure 6:
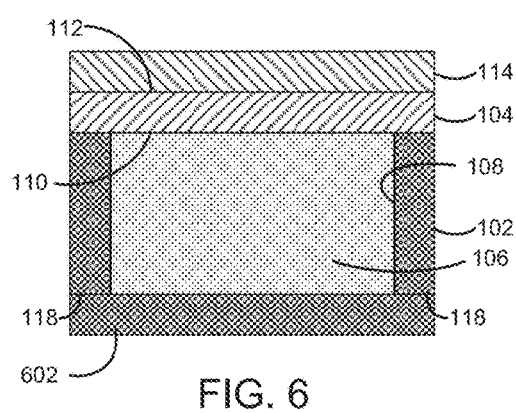
FIG. 6 is a graphic illustration of another fabrication stage of the drug delivery system of FIG. 1.

At 208, drug 106 is disposed within cavity 108, and cavity 108 pressurized and hermetically sealed. In FIG. 6, cavity 108 is sealed with a material 602, which may be substantially similar to a material of substrate 102.

Drug 106 may be disposed within cavity 108 by direct microinjection using one or more conventional micro-injection techniques.

Alternatively, or additionally, drug 106 may drug may be disposed within cavity 108 with a nebulization process. Referring to FIG. 5, the nebulization process may include masking exposed portions 118 of substrate 102 with a protective shadow mask. A drug solution may be supersaturated or concentrated at a solubility limit, and aerosolized into relatively fine droplets using a jet nebulizer. As the droplets accumulate on the shadow mask and within cavity 108, solvent within the droplets evaporates, leaving behind a film of drug crystals. The nebulizing process may continue until a desired drug mass is provided within cavity 108. The shadow mask may then be removed.

One or more agents 116 (FIG. 1) may be applied to an inner surface of material 602 prior to sealing cavity 108.

Cavity 108 may be pressurized prior to sealing cavity 108. For example, pressurization of cavity 108 may be achieved by hermetically sealing cavity 108 in a pressurized atmosphere.

Cavity 108 may be pressurized subsequent to sealing of cavity 108. For example, pressurization of cavity 108 can be achieved by hermetically sealing cavity 108 under relatively low-temperature conditions. Pressurization then ensues with expansion of gas within cavity 108 when warmed to ambient and/or body temperature. A specific pressure and/or temperature at which cavity 108 is hermetically sealed may be selected based on a desired rupture pressure and rupture threshold.

Air transport through metal is relatively negligible and may be further reduced and/or minimized by sealing cavity 108 within a high molecular weight inert gas atmosphere, such as argon or xenon.

Cavity 108 may be sealed using one or more of a variety of types of sealants, which may include a conventional silicon adhesive, such as an epoxy and/or a crystal-bonding sealant, and/or a low-temperature ultrasound-assisted bonding technique.

Method 200 may be implemented to form a plurality of cavities within a shared substrate, and may include cutting or dicing the substrate into multiple substrates, each including one or more drug-containing cavities, such as described above.

Where method 200 is implemented to form a plurality of cavities, different drugs and/or combinations of drugs may be disposed within different cavities at 208, such as with one or more masking procedures. Similarly, diaphragms having different rupture thresholds may be disposed over different cavities. The substrate may be cut to provide a substrate having multiple cavities, which may include different drugs or combinations of drugs, and/or different rupture thresholds.

Figure 7:
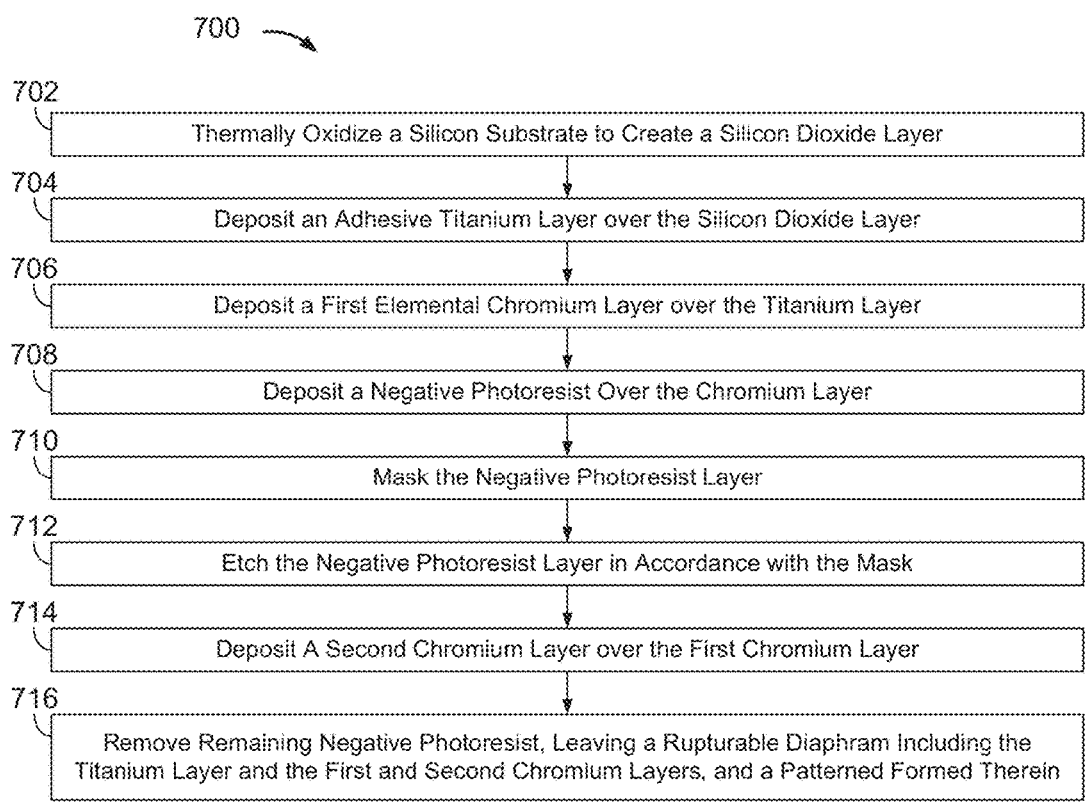
FIG. 7 is a flowchart of a method of fabricating a pressure-rupturable diaphragm.

FIG. 7 is a flowchart of a method 700 of fabricating a pressure-rupturable diaphragm. Method 700 is described below with reference to example materials for illustrative purposes. Method 700 is not, however, limited to the example materials described below.

Method 700 is further described with reference to FIG. 8, which is a graphic illustration of a progression of fabrication stages of a pressure-rupturable diaphragm. Method 700 is not, however, limited to the example of FIG. 8.

At 702, a polished silicon wafer 802 is thermally oxidized to create a silicon dioxide layer 804.

At 704, an adhesive titanium layer 806 is deposited over silicon dioxide layer 804. Titanium layer 806 may be deposited by electron-beam evaporation under high vacuum, and may have a thickness within a range of approximately 5-30 nanometers (nm).

At 706, an elemental chromium layer 808 is deposited onto titanium layer 806. Chromium layer 808 may be deposited by electron-beam evaporation under high vacuum, and may have a thickness within a range of approximately 50-120 nm.

At 708, a negative photoresist 810 is deposited onto chromium layer 808. Negative photoresist 810 may be spin deposited, and may have a thickness in excess of 1000 nm.

Figure 8:
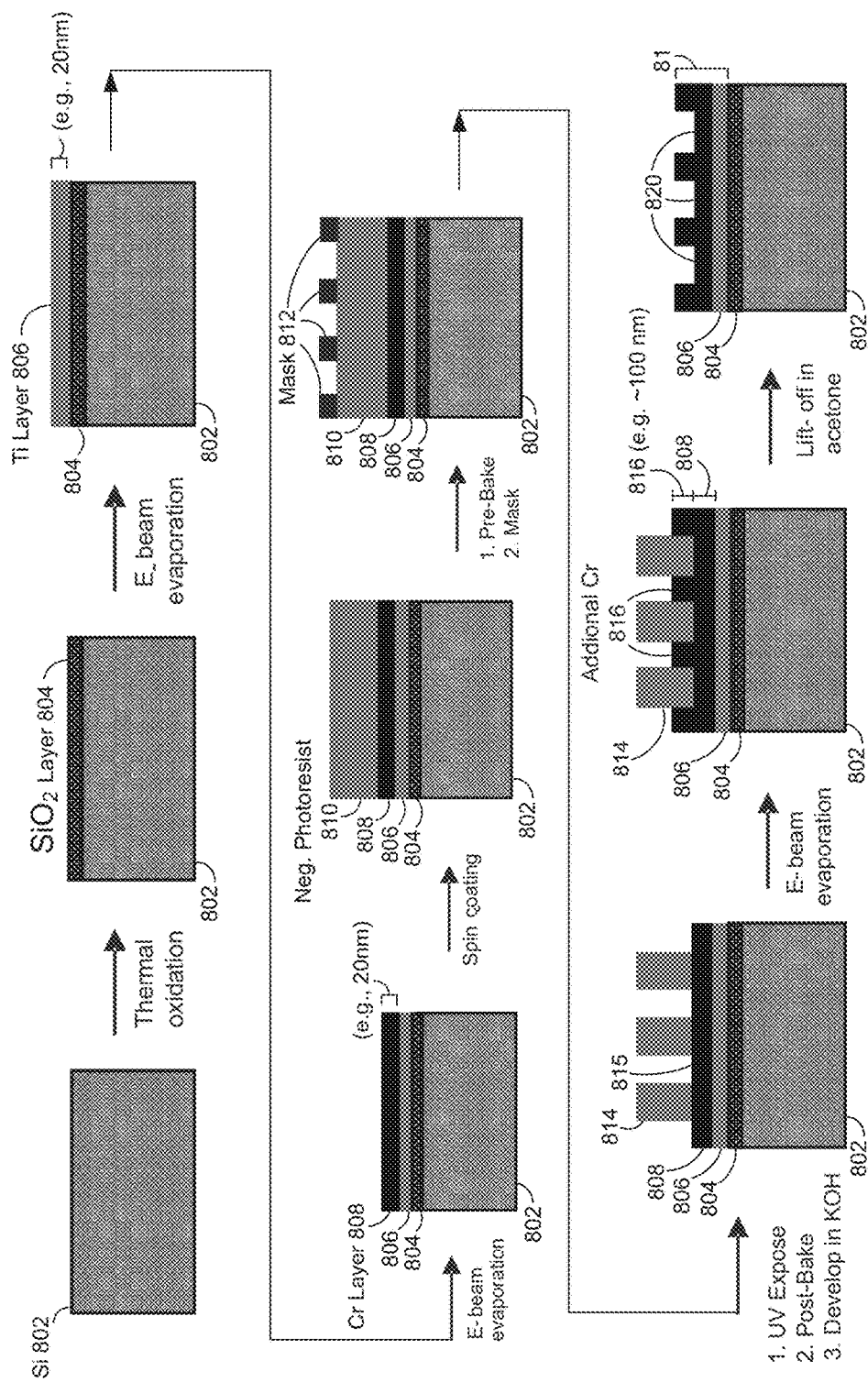
FIG. 8 is a graphic illustration of a progression of fabrication stages of a pressure-rupturable diaphragm.

At 710, portions of negative photoresist 810 are masked (see mask 812 in FIG. 8).

At 712, one or more features and/or patterns of features are photolithographically etched in negative photoresist 810, based on the masking at 710. The features may include walls 814 extending from chromium layer 808 defining trenches 815 therebetween.

At 714, a second chromium layer 816 is deposited over chromium layer 808. Second chromium layer 816 may be deposited by electron-beam evaporation, and may have a thickness within a range of approximately of 30-50 nm. Chromium layers 808 and 816, together, may have a minimum thickness of approximately 80 nm.

At 716, remaining portions of photoresist 810, such as walls 814, are removed from chromium layers 808 and 816, leaving a rupturable diaphragm 818, including titanium layer 806 and chromium layers 808 and 816, and having a pattern of grooves 820 formed therein.

Figure 9:
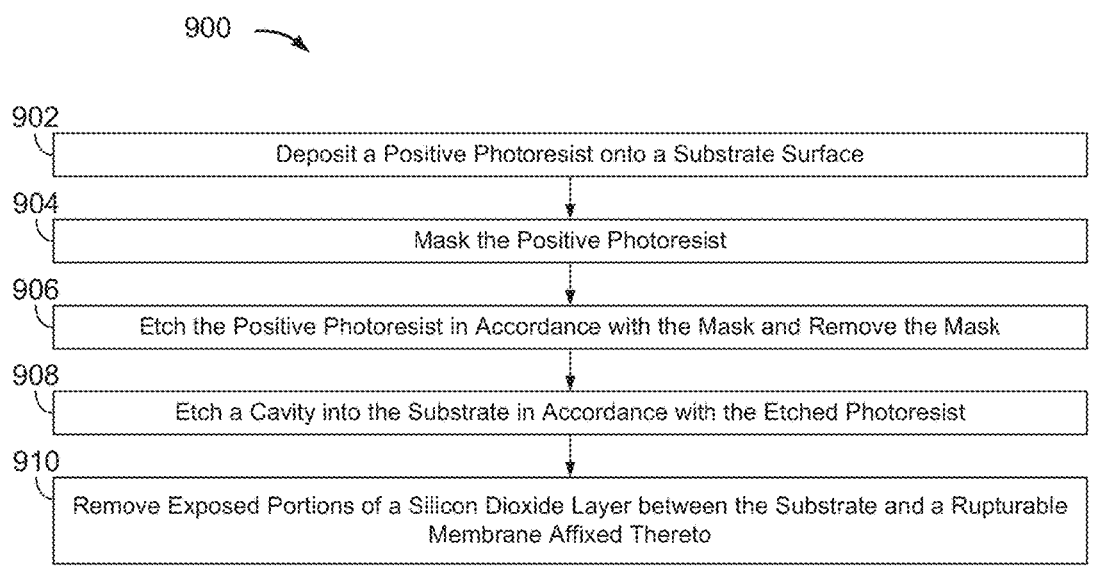
FIG. 9 is a flowchart of a method of fabricating a drug cavity.

FIG. 9 is a flowchart of a method 900 of fabricating a drug cavity. Method 900 is described below with reference to example materials for illustrative purposes. Method 900 is not, however, limited to the example materials described below.

Figure 10:
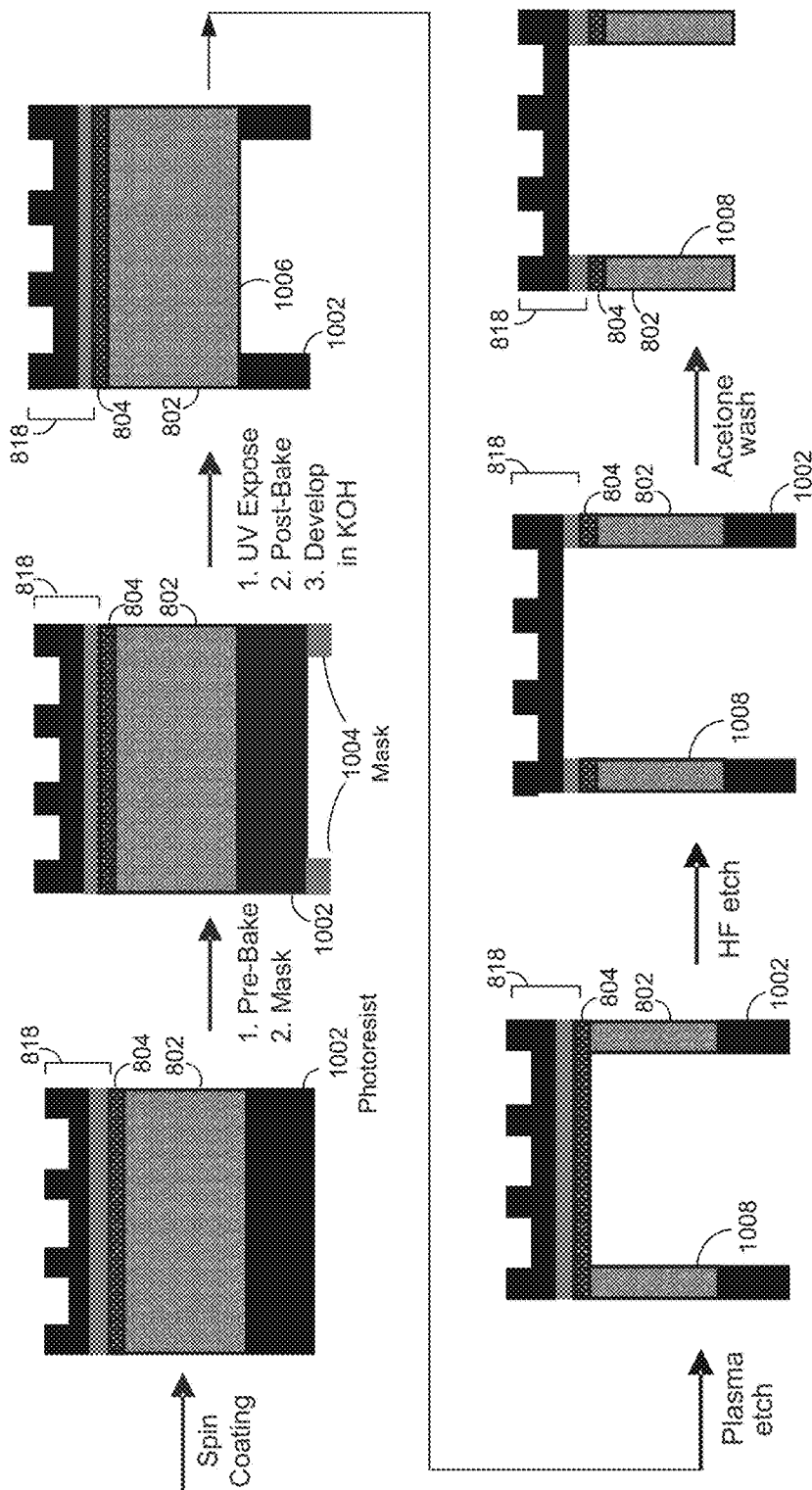
FIG. 10 is a graphic illustration of a progression of fabrication stages of a drug cavity.

Method 900 is further described with reference to FIGS. 8 and 10. FIG. 10 is a graphic illustration of a progression of fabrication stages of a drug cavity. Method 900 is not, however, limited to the examples of FIGS. 8 and 10.

At 902, a positive photoresist 1002 is spun onto a surface of substrate 802.

At 904, positive photoresist 1002 is masked with a mask 1004.

At 906, positive photoresist 1002 is etched in accordance with mask 1004 to expose a portion 1006 of the surface of substrate 802, and mask 1004 is removed.

At 908, a cavity 1008 is etched into substrate 802 through exposed portion 1006 of substrate 802.

Up to this point, silicon dioxide layer 804 may structurally support diaphragm 818.

At 910, exposed portions of silicon dioxide layer 804 are removed, such as with a wet-etching process, which may utilize hydrofluoric acid to remove release diaphragm 804 from silicon dioxide layer 804.

Referring back to 906, positive photoresist 1002 may be etched to create one or more physical features or shapes such as, for example, lines, circles, ellipses, and/or one or more polygons. At 908, substrate 802 may be etched in accordance with the one or more physical features or shapes of positive photoresist 1002 until silicon dioxide layer 804 is reached, such as with an STS-DRIE silicon etching technique, to leave one or more "residual posts" of substrate material within cavity 1008. At 910, silicon dioxide layer 804 may be wet-etched to retain corresponding residual posts.

The residual posts may serve to anchor and/or stiffen diaphragm 818. A rupture threshold, rupture site, rupture pattern, and/or rupture time of diaphragm 818 may be defined, at least in part, by the residual posts.

In the example of FIG. 10, cavity 1008 is formed in substrate 802 through a surface of substrate 802 that is opposite diaphragm 818. Alternatively, cavity 1008 may be formed through another surface of substrate 802, such as a surface adjacent to diaphragm 818.

Figure 11:
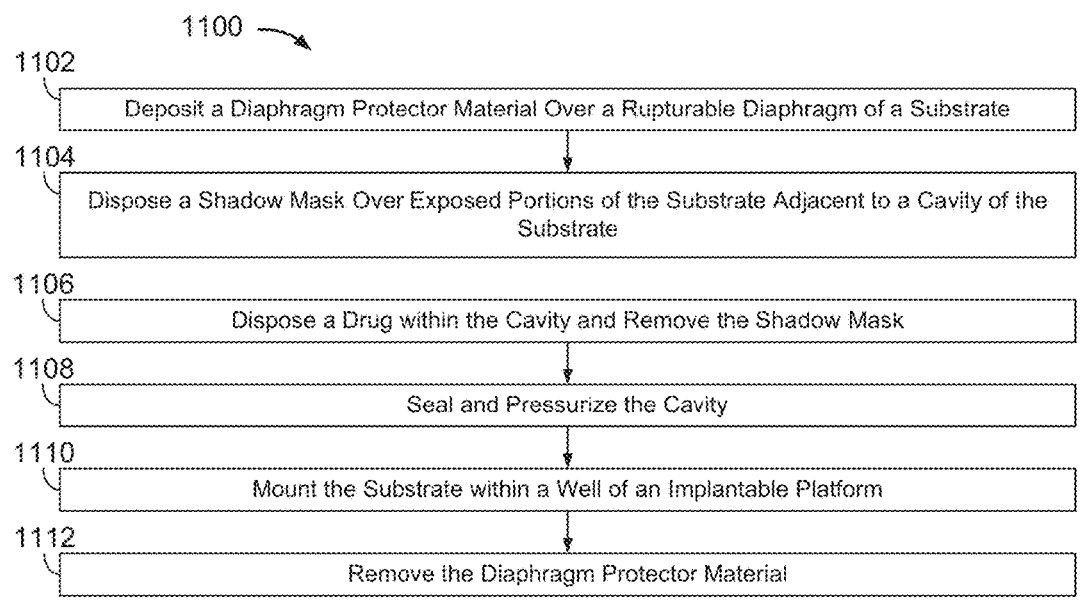
FIG. 11 is a flowchart of a method of disposing a diaphragm protector over a diaphragm, disposing a drug within a cavity, and sealing the cavity.

FIG. 11 is a flowchart of a method 1100 of disposing a diaphragm protector over a diaphragm, disposing a drug within a cavity, and sealing the cavity. Method 1100 is described below with reference to example materials for illustrative purposes. Method 1100 is not, however, limited to the example materials described below.

Figure 12:
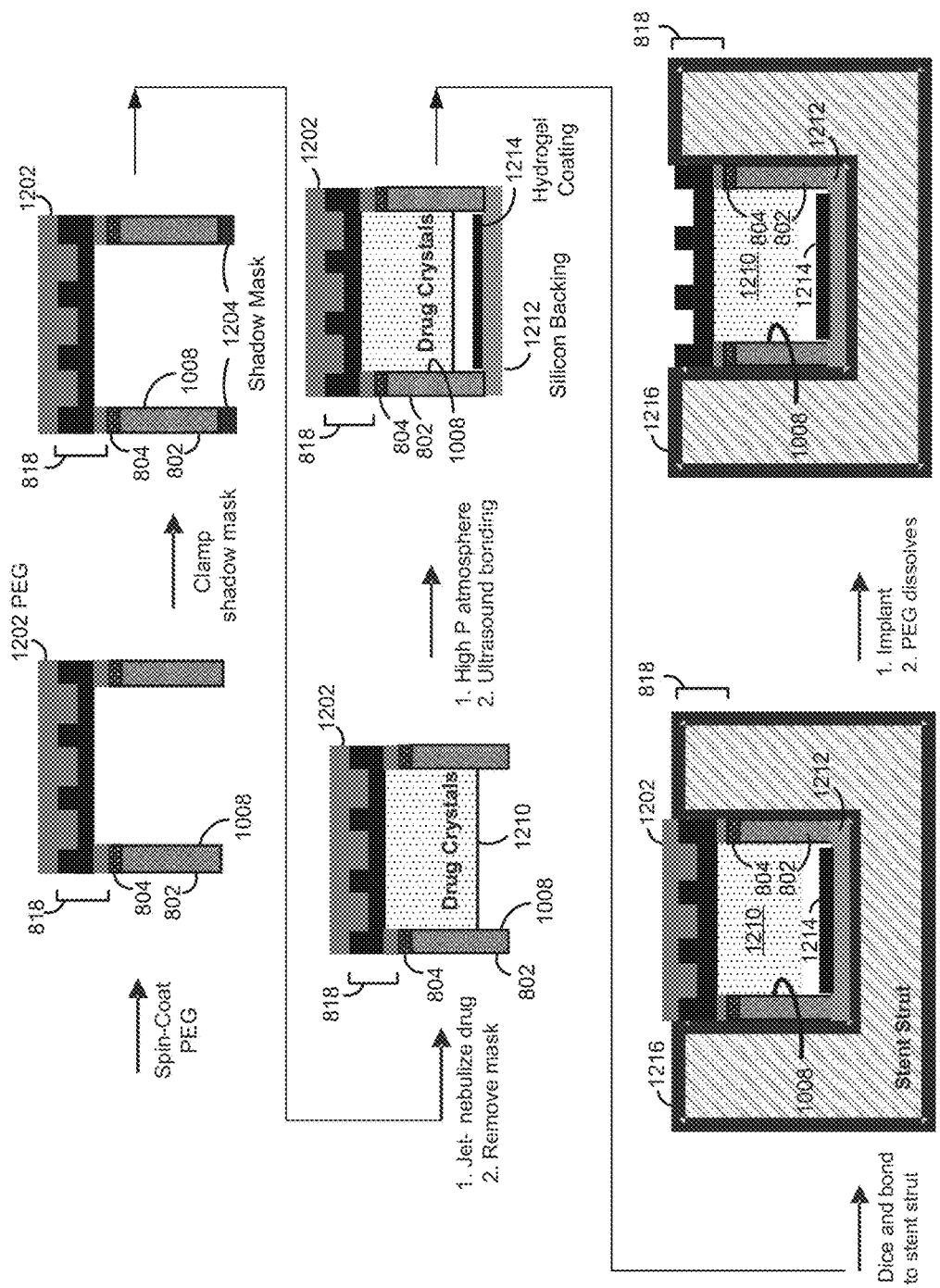
FIG. 12 is a graphic illustration of a progression of stages of disposing a diaphragm protector over a diaphragm, disposing a drug within a cavity, and sealing the cavity.

Method 1100 is further described with reference to FIGS. 8, 10, and 12. FIG. 12 is a graphic illustration of a progression of stages of disposing a diaphragm protector over a diaphragm, disposing a drug within a cavity, and sealing the cavity. Method 1100 is not, however, limited to the examples of FIGS. 8, 10, and 12.

At 1102, a layer 1202 of a diaphragm protector material, such as polyethylene glycol (PEG), is spun onto diaphragm 818. Layer 1202 may be spun to a thickness of greater than 10 um.

At 1104, a shadow mask 1204 is disposed over exposed portions of substrate 802.

At 1106, a drug 1210 is disposed within cavity 1008, such as by nebulization. Shadow mask 1204 is then removed.

At 1108, cavity 1008 is hermetically sealed with a substrate material 1212, such as described in one or more examples above. Substrate material 1212 may include an agent 1214, applied and/or affixed to an inner surface of substrate material 1212. Agent 1214 may include a hydrogel, such as described in one or more examples above.

Cavity 1008 may be pressurized and/or evacuated, such as described in one or more examples herein.

At 1110, substrate 802, including diaphragm 818, diaphragm protector layer 1202, drug 1210, substrate material 1212, and agent 1214, is mounted within a well of an implantable platform 1216, which may include a stent.

Where substrate 802 includes a plurality of drug-containing cavities 1008, the substrate may be cut into a plurality of substrates, each of which may include one or more cavities 1008, and which may mounted within a well of implantable platform 1216.

At 1112, platform 1216 is implanted and diaphragm protector layer 1202 dissolves, degrades, and/or otherwise dissipates within the implant environment.

Figure 13:
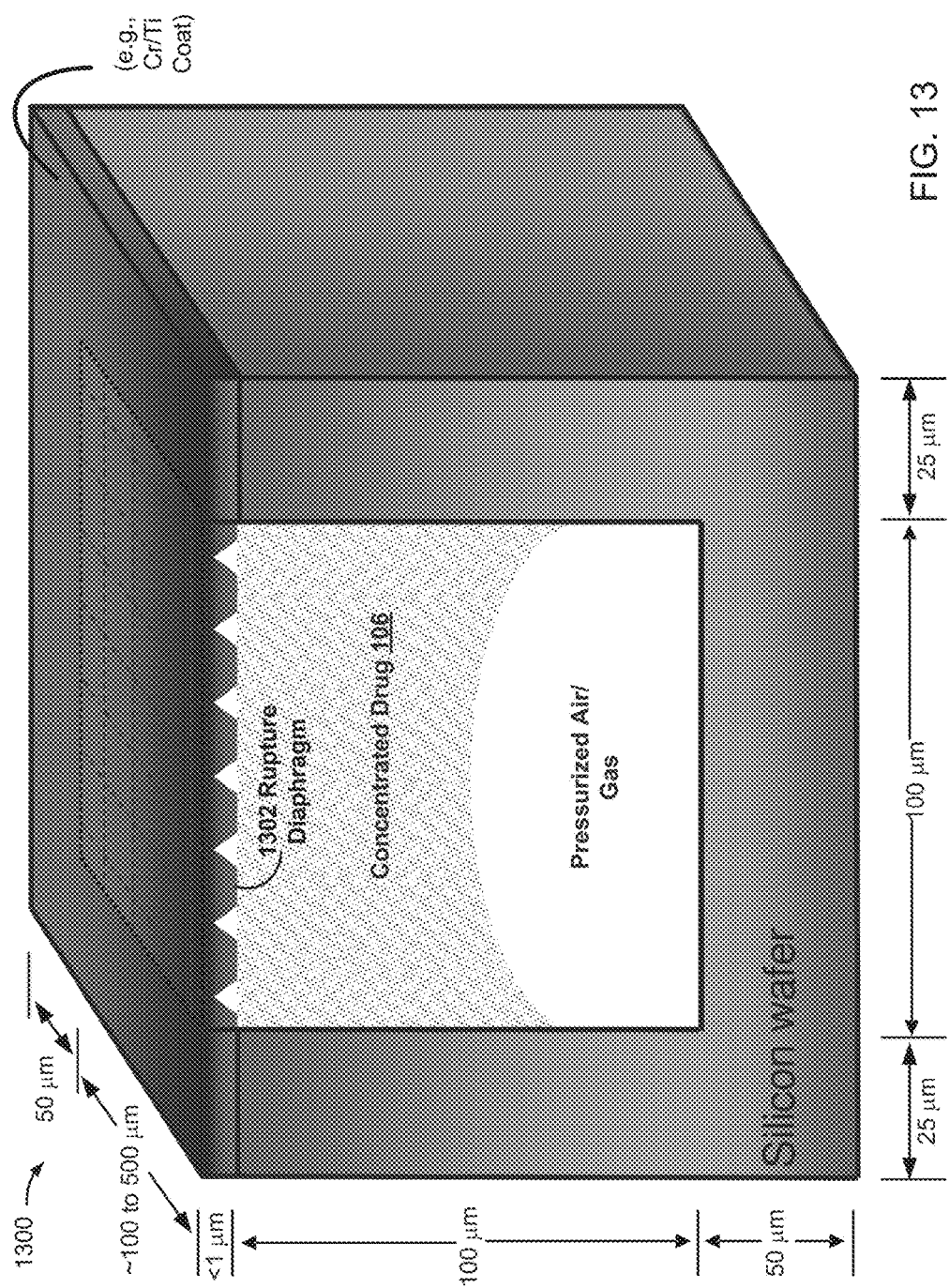
FIG. 13 is a block diagram of another drug delivery system, including example dimensions.

FIG. 13 is a block diagram of a drug delivery system 1300 to illustrate an example pattern formed within a surface of a rupturable diaphragm 1302. For illustrative purposes, FIG. 13 includes example dimensions. Methods and systems disclosed herein are not, however, limited to example dimensions disclosed herein.

Figure 14:
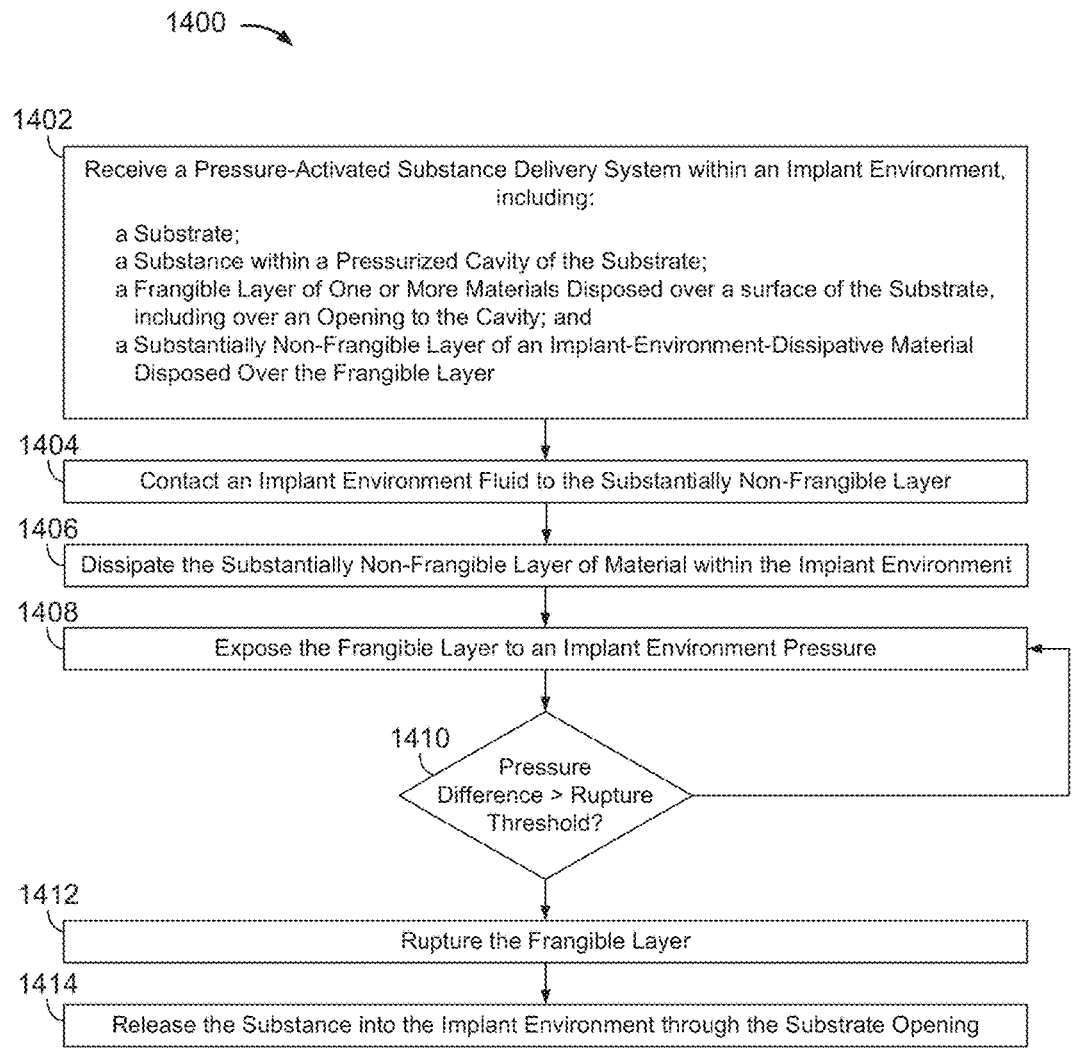
FIG. 14 is a flowchart of a method of using an implantable pressure-actuated substance delivery system.

FIG. 14 is a flowchart of a method 1400 of using an implantable pressure-actuated substance delivery system.

At 1402, a substance delivery system is received within an implant environment. The substance delivery system may include:

a substrate;
a substance within a pressurized cavity of the substrate;
a frangible layer of one or more materials disposed over a surface of the substrate, including over an opening to the cavity; and
a substantially non-frangible layer of an implant-environment-dissipative material disposed over the frangible layer.

At 1404, an implant environment fluid is contacted to the substantially non-frangible layer within the implant environment.

At 1406, the substantially non-frangible layer is dissipated within the implant environment in response to the contacting of the implant environment fluid.

At 1408, the frangible layer of material is exposed to an implant environment pressure in response to the dissipating of the substantially non-frangible layer.

At 1410, when a difference between the implant environment pressure and the cavity pressure does not exceeds a rupture threshold of the frangible layer, integrity of the frangible layer is maintained at 1408. When the rupture threshold is exceeded, processing proceeds to 1412.

At 1412, the frangible layer is ruptured.

At 1414, the substance is released from the cavity into the implant environment through the substrate opening.

The substance delivery system may include a drug, such as described in one or more examples herein, which may include an anti-clotting agent. A method of using a drug delivery system is described below with reference to FIG. 15.

The substance delivery system may include one or more a sensory agent to invoke or elicit a sensory perception in patient, and a hydrogel, such as described in one or more examples herein. A method of using such a substance delivery system is described further below with reference to FIG. 16.

Figure 15:
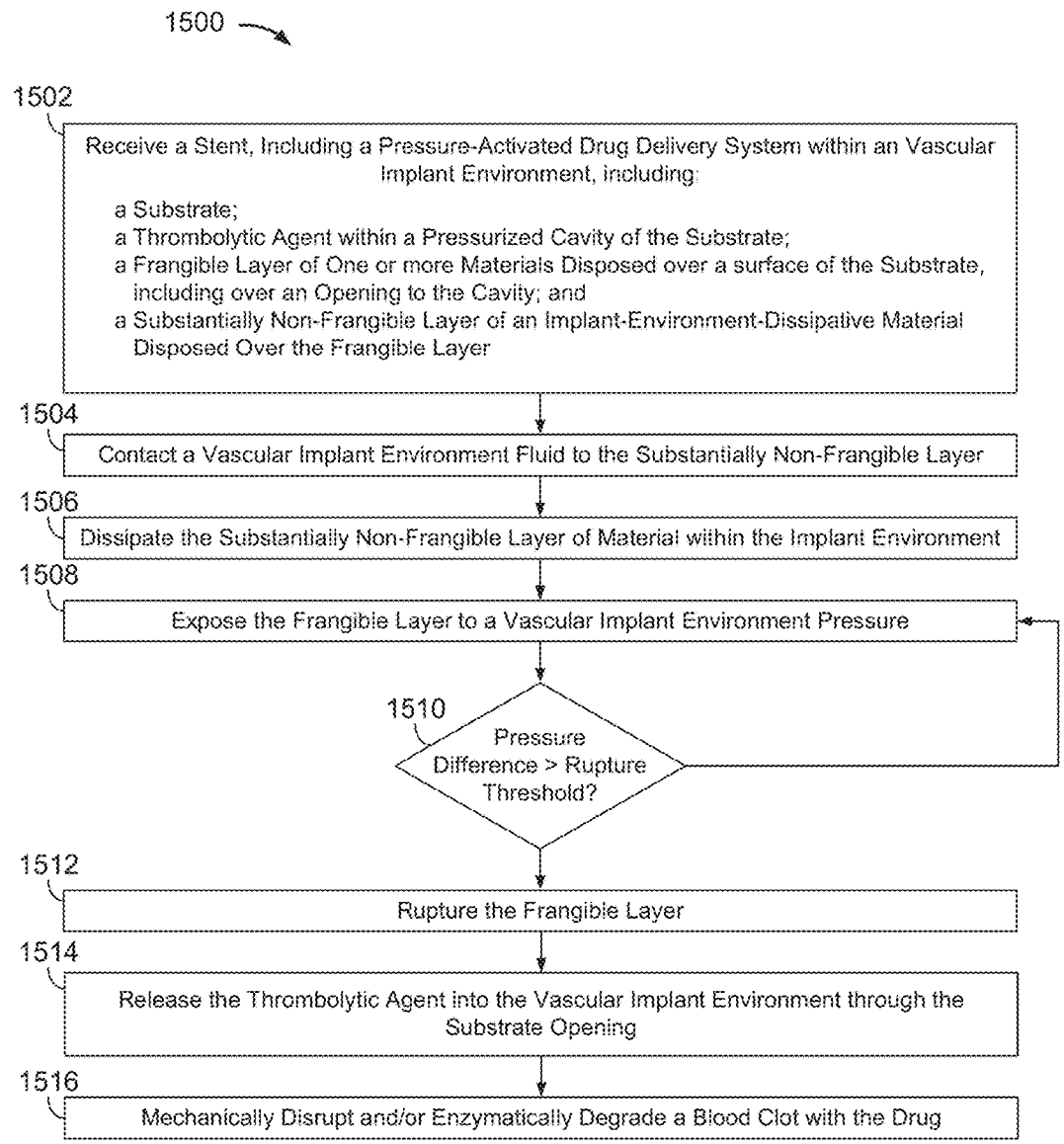
FIG. 15 is a flowchart of a method of using an implantable pressure-actuated drug delivery system within a vascular implant environment to treat a potential blood clot.

FIG. 15 is a flowchart of a method 1500 of using an implantable pressure-actuated drug delivery system within a vascular implant environment to treat a potential blood clot.

At 1502, a drug delivery system is received within a vascular implant environment.

The vascular implant environment may include one or more of a coronary vascular implant environment and a non-coronary or peripheral vascular implant environment.

The drug delivery system may be received as an implantable platform, which may include a stent and/or a stand-lone drug delivery platform.

The drug delivery system may include:
a substrate;
a thrombolytic drug or agent within a pressurized cavity of the substrate;
a frangible layer of one or more materials disposed over a surface of the substrate, including over an opening to the cavity; and
a substantially non-frangible layer of an implant-environment-dissipative material disposed over the frangible layer.

At 1504, a vascular implant environment fluid is contacted to the substantially non-frangible layer within the vascular implant environment.

At 1506, the substantially non-frangible layer is dissipated within the vascular implant environment in response to the contacting of the vascular implant environment fluid.

At 1508, the frangible layer of material is exposed to an vascular implant environment pressure (e.g., vascular blood pressure), in response to the dissipating of the substantially non-frangible layer.

At 1510, when a difference between the vascular implant environment pressure and the cavity pressure does not exceeds a rupture threshold of the frangible layer, integrity of the frangible layer is maintained at 1408. When the rupture threshold is exceeded, processing proceeds to 1512.

At 1512, the frangible layer is ruptured.

At 1514, the thrombolytic agent is released from the cavity into the vascular implant environment through the substrate opening.

Figure 16:
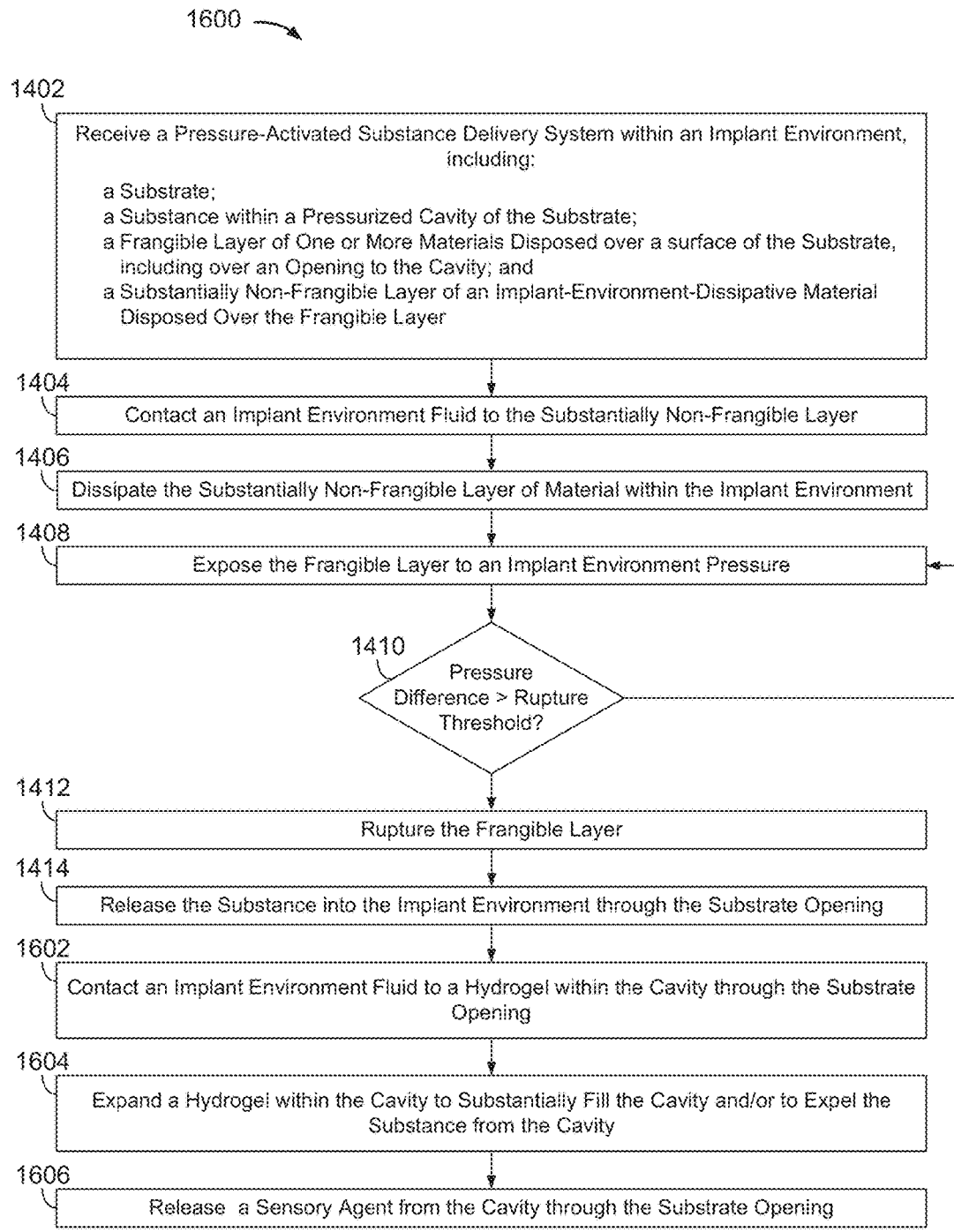
FIG. 16 is a flowchart of a method of using an implantable pressure-actuated substance delivery system that includes one or more of a hydrogel and a sensory agent.

FIG. 16 is a flowchart of a method 1600 of using an implantable pressure-actuated substance delivery system that includes one or more of a hydrogel and a sensory agent.

Method 1600 includes features 1402 through 1414 of method 1400, and may include one or more of features 1602 through 1606.

At 1602, an implant environment fluid is contact to a hydrogel within the substrate cavity. The implant environment fluids of 1404 and 1604 may be the same fluid or different fluids within the implant environment.

At 1604, the implant environment fluid of 1604 is absorbed by the hydrogel to expand the hydrogel within the cavity.

At 1606, a sensory agent is released from the substrate cavity into the implant environment to invoke or elicit a sensory perception in the patient, such as described in one or more examples herein.

Methods and systems are disclosed herein with the aid of functional building blocks illustrating the functions, features, and relationships thereof. At least some of the boundaries of these functional building blocks have been arbitrarily defined herein for the convenience of the description. Alternate boundaries may be defined so long as the specified functions and relationships thereof are appropriately performed.

While various embodiments are disclosed herein, it should be understood that they have been presented by way of example only, and not limitation. It will be apparent to persons skilled in the relevant art that various changes in form and detail may be made therein without departing from the spirit and scope of the methods and systems disclosed herein. Thus, the breadth and scope of the claims should not be limited by any of the example embodiments disclosed herein.

What is claimed is:

1. A method of fabricating an implantable, pressure-actuated drug delivery system, the method comprising:
fabricating a frangible layer of one or more materials over a substrate surface;
forming a cavity within the substrate, including an opening through the substrate surface to expose at least a portion of the frangible layer to the cavity;
disposing a drug within the cavity;
sealing the cavity;
pressurizing the cavity; and
fabricating a substantially non-frangible layer of an implant-environment-dissipative material over the frangible layer to prevent premature rupture of the frangible layer an at an ambient environment pressure and to dissipate within an implant environment,
wherein the frangible layer is fabricated to have a rupture threshold within a range of approximately 200 millimeters of mercury (mmHg) to 1200 mmHg, and a rupture time of at least 15 seconds, and
wherein the pressurized cavity is pressurized to a pressure that exceeds the rupture threshold by a rupture pressure within a range of approximately 20 mmHg to 50 mmHg relative to one atmosphere to cause the frangible layer to rupture when the implant environment pressure falls below and remains below the rupture pressure for at least 15 seconds.

2. The method of claim 1, wherein the fabricating of the frangible layer includes:

controlling the thickness of the frangible layer;

wherein one or more of the rupture threshold, a rupture site, a rupture pattern, and a rupture time of the frangible layer are functions of the thickness.

3. The method of claim 1, further including one or more of:

forming a pattern within a surface of the frangible layer, wherein one or more of the rupture threshold, a rupture site, rupture pattern, and a rupture time of the frangible layer are functions of the pattern within the surface of the frangible layer; and retaining a patterned portion of the substrate within the cavity and in contact with the frangible layer during the forming of the cavity, wherein one or more of the rupture threshold, a rupture site, a rupture pattern, and a rupture time of the frangible layer are functions of the pattern within the cavity.

4. The method of claim 1, wherein pressurizing of the cavity includes one or more of:

performing the sealing of the cavity within a pressurized environment;

performing the sealing of the cavity within a low temperature environment, wherein the cavity pressure increases as the sealed cavity warms; and performing the sealing of the cavity within a high molecular weight inert gas atmosphere.

5. The method of claim 1, wherein the disposing of the drug within the cavity includes:

disposing the drug as an aerosol.

6. The method of claim 1, further including:

mounting the drug delivery system within an implantable platform, including one or more of a coronary stent, a peripheral stent, and a substrate-specific platform.

7. The method of claim 1, wherein the disposing of the drug includes disposing a thrombolytic drug within the cavity.

8. The method of claim 1, wherein the frangible layer is fabricated such that triggering the rupture of the frangible layer is accomplished without external sensory or control intervention.

9. The method of claim 1 wherein the frangible layer is fabricated such that triggering the rupture of the frangible layer is based on a change in environmental pressure external to the frangible layer exceeding the rupture threshold.

10. The method of claim 9, wherein the change in environmental pressure is a change in blood pressure.

* * * * *